United States Patent
Fujino et al.

(10) Patent No.: US 12,343,678 B2
(45) Date of Patent: Jul. 1, 2025

(54) NITROGEN RECOVERY METHOD, NITROGEN RECOVERY DEVICE, AND PRODUCT OBTAINED BY SAME

(71) Applicant: JFR CO., LTD., Tokyo (JP)

(72) Inventors: Akira Fujino, Tokyo (JP); Yuko Sasagawa, Tokyo (JP); Junichi Morota, Shizuoka (JP)

(73) Assignee: JFR CO., LTD., Tokyo (JP)

( * ) Notice: Subject to any disclaimer, the term of this patent is extended or adjusted under 35 U.S.C. 154(b) by 560 days.

(21) Appl. No.: 17/642,368

(22) PCT Filed: Sep. 11, 2020

(86) PCT No.: PCT/JP2020/034429
§ 371 (c)(1),
(2) Date: Mar. 11, 2022

(87) PCT Pub. No.: WO2021/049603
PCT Pub. Date: Mar. 18, 2021

(65) Prior Publication Data
US 2022/0323901 A1    Oct. 13, 2022

(30) Foreign Application Priority Data

Sep. 13, 2019  (JP) ................. 2019-166997

(51) Int. Cl.

| | | |
|---|---|---|
| *C12N 1/20* | (2006.01) | |
| *B01D 53/58* | (2006.01) | |
| *B01D 53/84* | (2006.01) | |
| *C12M 1/00* | (2006.01) | |
| *C12M 1/12* | (2006.01) | |
| *C12M 1/34* | (2006.01) | |
| *C12N 11/14* | (2006.01) | |
| *C12P 3/00* | (2006.01) | |

(52) U.S. Cl.
CPC ............ *B01D 53/58* (2013.01); *B01D 53/84* (2013.01); *C12M 25/18* (2013.01); *C12M 29/06* (2013.01); *C12M 29/26* (2013.01); *C12M 41/26* (2013.01); *C12M 47/10* (2013.01); *C12N 1/20* (2013.01); *C12N 11/14* (2013.01); *C12P 3/00* (2013.01)

(58) Field of Classification Search
CPC ............ C12N 1/20; C12N 11/16; C12P 13/00
See application file for complete search history.

(56) References Cited

U.S. PATENT DOCUMENTS

2024/0166988 A1* 5/2024 Sasagawa ................. C02F 3/34

FOREIGN PATENT DOCUMENTS

| | | |
|---|---|---|
| JP | H724247 A | 1/1995 |
| JP | 2000600 A | 1/2000 |
| JP | 2002153721 A | 5/2002 |
| JP | 2004195440 A | 7/2004 |
| JP | 2004358370 A | 12/2004 |
| JP | 2005161258 A | 6/2005 |
| JP | 2008239466 A | 10/2008 |
| JP | 2011240254 A | 12/2011 |
| JP | 201418779 A | 2/2014 |
| JP | 5742195 B2 | 7/2015 |
| JP | 2018130705 A | 8/2018 |

OTHER PUBLICATIONS

Nitrification Process: Principles of Biological Denitrification and Denitrification and Water Quality Management Nitrification, https://web.archive.org/web/20180310195801/, https://mizusyoli.com/dattitu/entry43.html, Mar. 10, 2018, 6 pages.
Office Action issued on Mar. 12, 2024, in corresponding Japanese Application No. 2021545610, 3 pages.
International Search Report (with English Translation) and Written Opinion (with Machine Translation) issued on Nov. 2, 2020 in corresponding International Patent Application No. PCT/JP2020/034429; 12 pages.

* cited by examiner

*Primary Examiner* — Tekchand Saidha
(74) *Attorney, Agent, or Firm* — Maier & Maier, PLLC

(57) ABSTRACT

This nitrogen recovery method is for causing nitrifying bacteria to decompose an ammonia component in an ammonia-containing gas, and recovering a nitrogen component contained in ammonia as an ammonia gas decomposition product, involving: supplying circulating water to a microorganism decomposition tank retaining a nitrifying bacterium carrier carrying nitrifying bacteria to maintain the carrier wet; passing ammonia-containing gas through the carrier in the wet state in an oxygen-containing atmosphere; dissolving an ammonia component in the ammonia-containing gas in the circulating water, together with an ammonia gas decomposition product produced by the nitrifying bacteria, to continue decomposing the ammonia-containing gas while the decomposition product is accumulated in the circulating water; and collecting all or a portion of the circulating water to recover the ammonia gas decomposition product, when the concentration of nitrate ion as an ammonia decomposition product in the circulating water reaches a predetermined concentration of 5000 mg/L or more.

11 Claims, 1 Drawing Sheet

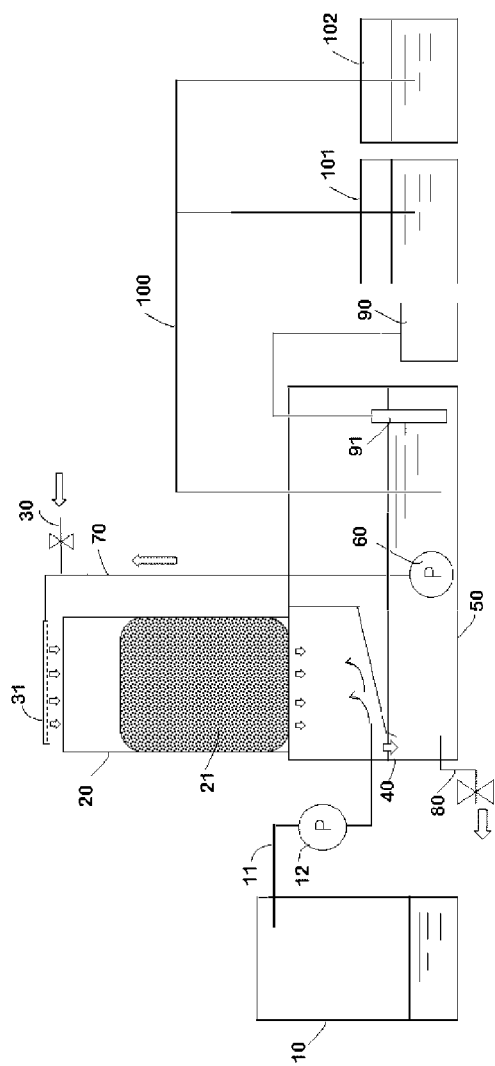

NITROGEN RECOVERY METHOD, NITROGEN RECOVERY DEVICE, AND PRODUCT OBTAINED BY SAME

TECHNICAL FIELD

The present invention relates to a nitrogen recovery method, a nitrogen recovery device and a product obtained by the same. More specifically, the present invention relates to a nitrogen recovery method and a nitrogen recovery device for recovering nitrogen with high efficiency from ammonia gas generated in e.g., livestock production facilities, compost depot and sewage treatment plants, and a product obtained by the same.

BACKGROUND ART

An offensive odor, which has ammonia as a main component, has been generated in e.g., livestock farms, composting facilities and raw sewage treatment plants, and the problems of complaints from neighborhood about the offensive odor, and health problems of workers in the fields have often occurred. Therefore, it is required to treat the generated ammonia gas by a deodorization device, and deodorization using agents, adsorption deodorization using adsorbents, deodorization by combustion, and biological deodorization have been performed. However, the above deodorization cannot be a basic solution because costs are required to treat used agents and dispose of adsorbents, and gas with a high environmental burden such as NOx is discharged after deodorization.

Biological deodorization using nitrifying bacteria, which decompose ammonia by oxidizing it to nitrous acid and further nitric acid, for example, has been widely used as a measure for an offensive odor contained in ammonia generated from e.g., livestock production facilities, compost depot, and sewage treatment plants. However, many of such deodorization devices are provided with a part for a denitrification step of decomposing nitrous acid and nitric acid remaining in the devices into nitrogen gas, and thus are large and require high costs. In addition, even if ammonia is successfully decomposed and environmental pollution can be prevented, it has not been possible to effectively utilize nitrogen.

As a technique for decomposing ammonia gas with an offensive odor generated in a large amount from e.g., livestock production facilities, compost depot, and sewage treatment plants into nitric acid using nitrifying bacteria, the following has been known so far.

Patent Document 1, for example, proposes a deodorization and denitrification device, which is used for the nitrification and sulfur denitrification reactions of ammonia, and includes a deodorization tank packed with a deodorizing material having activated sludge added, and a water supply tank, which supplies water containing sodium thiosulfate to the deodorization tank. In the technique described in Patent Document 1, ammonia is removed, and also accumulations of inorganic nitrogen in circulating water can be suppressed by combining sulfur denitrification and nitrification reactions, and ammonia gas can be deodorized over a long period of time. Patent Document 1, however, is a technique in which thiosulfuric acid, and nitrous acid and nitric acid generated in the deodorization tank react, thiosulfuric acid is oxidized to generate sulfuric acid, and inorganic nitrogen in nitrous acid and nitric acid is removed as nitrogen gas. The technique is not intended to recover or effectively utilize ammoniacal nitrogen.

In addition, Patent Document 2 proposes a packed type biological deodorizing tower, which intermittently sprays circulating water to a packed layer, which is packed with a microorganism carrier, and washes ammonium nitrate and ammonium nitrite, which the ammonium nitrate and ammonium nitrite are generated by chemical reaction between nitrate group and nitrite group, and ammonia in gas, and are accumulated in the carrier, which the nitrate group and nitrite group are generated by the nitrification reaction of ammonia in gas by microorganisms. The tower is characterized in that the pH value of circulating water is kept to 7.5 or less by adding acid to the circulating water, and the concentration of ammoniacal nitrogen in the circulating water is controlled to 1000 mg-N/L or less. In Patent Document 2, in order to prevent a reduction in the nitrification rate of ammonia by microorganisms with an increase in the concentration of ammoniacal nitrogen in circulating water, the concentration of ammoniacal nitrogen in circulating water is lowered by adding sulfuric acid to circulating water. As is the case of Patent Document 1, Patent Document 2 is not intended to recover or effectively utilize ammoniacal nitrogen.

Patent Document 3 proposes a method for treating an ammonia-containing gas, characterized in that ammonia gas is introduced into a microorganism carrier storage tank, which stores a microorganism carrier supporting ammonia-oxidizing bacteria to convert ammonia into nitrite, and also water is sprayed to the microorganism carrier storage tank to dissolve ammonia gas in the sprayed water, ammonia dissolved in water is oxidized to nitrogen in the form of nitrite by the ammonia-oxidizing bacteria, the sprayed water is recovered as circulating water, the concentrations of ammonium ion or/and nitrite nitrogen in the circulating water are adjusted to 500 mg/L or more and 650 mg/L or more, respectively, and the water is used for the water spraying. The concentration of ammonium ion or/and the concentration of nitrite nitrogen in the circulating water is adjusted to make the environment of the microorganism carrier storage tank suitable for ammonia-oxidizing bacteria and unsuitable for nitrite-oxidizing bacteria, and the activity of nitrite-oxidizing bacteria is inhibited while maintaining the activity of ammonia oxidizing-bacteria to stably convert ammonia into nitrogen in the form of nitrite. In the method the obtained nitrite nitrogen is then decomposed into nitrogen gas by denitrification treatment using anaerobic ammonia-oxidizing bacteria, denitrified utilizing denitrifying bacteria which are heterotrophic bacteria, and organic matter as an electron donor, or nitrate nitrogen is removed utilizing sulfamic acid. As is the cases of Patent Documents 1 and 2, the method described in Patent Document 3 is not intended to recover or effectively utilize ammoniacal nitrogen.

Patent Document 4 proposes a hydroponic culture device, characterized by being provided with an absorption tank in which ammonia generated by anaerobic decomposition of food waste is absorbed by a cultivation nutrient solution; a circulation device in which a cultivation nutrient solution which has absorbed ammonia is circulated in a cultivation nutrient solution tank for hydroponic culture; and hydroponic culture equipment having a cultivation nutrient solution tank. Ammonia accumulated in the cultivation nutrient solution is converted into nitric acid by nitrate bacteria which adheres to a porous carrier. In the hydroponic culture device described in Patent Document 4, however, ammonia generated by anaerobic decomposition of food waste is directly absorbed to the cultivation nutrient solution, and the obtained solution is used as a liquid fertilizer. Ammoniacal nitrogen is used as a fertilizer but is used at a low concentration, and thus it cannot be said that this utilization is efficiently effective.

Patent Document 5 proposes that ammonia gas is introduced into soil including e.g., nitrifying bacteria, corresponding to a nitrifying bacterium carrier, and an ammonia gas decomposition product by nitrifying bacteria (e.g., nitrate) is immobilized to soil. In the method described in Patent Document 5, however, nitrifying bacteria are allowed to exist in soil, and because of this, ammonia is oxidized and decomposed into nitrous acid or nitric acid, which is adsorbed in soil. It is also disclosed that soil for treating ammonia, to which nitrogen thus obtained is immobilized as inorganic nitrogen, is used as soil for plant cultivation; however, as described above, nitrifying bacteria to decompose ammonia exist in soil. Therefore, in order to utilize the soil for treating ammonia as *soli* for cultivation, nitrifying bacteria are removed from the production system and consumed every time, and thus it cannot be said that the method is efficient.

Furthermore, Patent Document 6 proposes a method for treating an ammoniacal nitrogen-containing liquid, including a nitrite partial formation tank, which includes an aeration unit and in which a liquid to be treated, containing at least ammoniacal nitrogen, is aerated in the presence of an ammonia-oxidizing bacteria; a denitrification tank in which the liquid to be treated, which has been treated in the nitrite partial formation tank, is treated in the presence of anaerobic ammonia-oxidizing bacteria to allow the ammoniacal nitrogen and nitrite nitrogen to react to cause conversion into nitrogen gas; an inorganic carbon component adjustment tank in which an inorganic carbon component is injected into the liquid to be treated, which is introduced into the denitrification tank, depending on the concentration of nitrite nitrogen in the liquid to be treated; and a pH adjustment tank in which a pH adjuster containing phosphorus is injected into the liquid to be treated, which is introduced into the denitrification tank, wherein the inorganic carbon component is injected into the liquid to be treated depending on the concentration of nitrite nitrogen in the liquid to be treated which is used for the denitrification step, and the pH of the liquid to be treated which is used for the denitrification step is adjusted with a pH adjuster containing phosphorus. The technique described in Patent Document 6 is a technique in which ammoniacal nitrogen and nitrite nitrogen, obtained by biodegradation of a liquid to be treated containing ammoniacal nitrogen, are allowed to efficiently react to obtain nitrogen gas, and is not intended to recover or effectively utilize ammoniacal nitrogen.

Patent Document 1: Japanese Unexamined Patent Application, Publication No. 2018-130705
Patent Document 2: Japanese Unexamined Patent Application, Publication No. H07-024247
Patent Document 3: Japanese Unexamined Patent Application, Publication No. 2005-161258
Patent Document 4: Japanese Unexamined Patent Application, Publication No. 2011-240254
Patent Document 5: Japanese Unexamined Patent Application, Publication No. 2000-000600
Patent Document 6: Japanese Patent No. 5742195

DISCLOSURE OF THE INVENTION

Problems to be Solved by the Invention

As described above, some methods have been proposed so far for decomposing ammonia gas for deodorization or detoxification to form nitrogen; however, such a method has not been established as to decompose an ammonia and to recover the obtained ammonia decomposition component at a high concentration to utilize the component effectively and efficiently.

Therefore, a subject of the present invention is to provide a novel nitrogen recovery method, nitrogen recovery device, and product such as a liquid fertilizer obtained by the same, which solve the problem as described above. Another subject of the present invention is to provide a nitrogen recovery method and a nitrogen recovery device for recovering a nitrogen component with high efficiency from ammonia gas generated in e.g., livestock production facilities, compost depot, and sewage treatment plants, and a product such as a liquid fertilizer obtained by the same.

Means for Solving the Problems

As a result of diligent investigations and researches to solve the problem, the present inventors have found that a nitrogen component can be recovered with high efficiency from ammonia gas by controlling the step of decomposing ammonia gas using nitrifying bacteria to recover a nitrogen component of the ammonia gas, in which the decomposition of ammonia gas by nitrifying bacteria is allowed to proceed continuously, and the nitrogen component can be accumulated simultaneously as nitric acid at a high concentration in circulating water which circulates in the system, thereby completing the present invention.

That is, the present invention to solve the problem is a nitrogen recovery method for recovering a nitrogen component contained in ammonia as an ammonia gas decomposition product by decomposing an ammonia component in an ammonia-containing gas using nitrifying bacteria, the method being characterized by supplying circulating water to a microorganism decomposition tank equipped with a nitrifying bacterium carrier supporting nitrifying bacteria to maintain the nitrifying bacterium carrier in a wet state; allowing the ammonia-containing gas to pass through the nitrifying bacterium carrier in the wet state under an oxygen-containing atmosphere; dissolving an ammonia component in the ammonia-containing gas in the circulating water, together with an ammonia gas decomposition product produced by the nitrifying bacteria, and continuing to decompose the ammonia-containing gas while accumulating the ammonia gas decomposition product in the circulating water; and collecting all or a portion of the circulating water to recover the ammonia gas decomposition product, when a concentration of nitrate ion as an ammonia decomposition product in the circulating water is increased to 5000 mg/L or more and reaches a predetermined concentration.

In an embodiment of the nitrogen recovery method in the present invention, the nitrifying bacterium carrier is an inorganic porous body and/or an inorganic fibrous body, e.g., glass foam. However, even if the carrier is made of organic matter, a porous body and a fibrous body from organic matter such as plastic, rubber or resin which does not generate an odor by decay can be used.

In another embodiment of the nitrogen recovery method in the present invention, the percentage of water content of the nitrifying bacterium carrier in the microorganism decomposition tank is 5% to 90%.

In yet another embodiment of the nitrogen recovery method in the present invention, the amount of circulating water supplied to the microorganism decomposition tank per 1 L of packed volume of the nitrifying bacterium carrier is 50 to 50000 mL/h. The "1 L of packed volume of the nitrifying bacterium carrier" indicates a volume amount of a nitrifying bacterium carrier when packing the nitrifying bacterium carrier in a 1 L container to a level container.

In yet another embodiment of the nitrogen recovery method in the present invention, circulating water is aerated so that the amount of aeration per 1 L of circulating water will be 0.5 to 10 L/min.

In yet another embodiment of the nitrogen recovery method in the present invention, circulating water is maintained at a pH of 5.0 to 9.0 and at a temperature of 10° C. to 60° C.

In one embodiment of the nitrogen recovery method in the present invention, nitrifying bacteria supported to the nitrifying bacterium carrier include ammonia-oxidizing bacteria (AOB) and nitrite-oxidizing bacteria (NOB).

In one embodiment of the nitrogen recovery method in the present invention, fresh circulating water is supplied to a system to resume decomposing the ammonia-containing gas after collecting all or a portion of the circulating water to recover the ammonia gas decomposition product when the concentration of nitrate ion as the ammonia decomposition product in the circulating water is increased to 5000 mg/L or more and reaches a predetermined concentration.

In one embodiment of the nitrogen recovery method in the present invention, all or a portion of the circulating water is collected to recover the ammonia gas decomposition product, when the concentration of nitrate ion in the circulating water is increased by 5000 mg/L or more from a concentration at a start point of allowing the ammonia-containing gas to pass through.

In one embodiment of the nitrogen recovery method in the present invention, the ammonia-containing gas is derived from manure disposing or sewage treatment facilities.

The present invention to solve the problem is achieved by a nitrogen recovery device for recovering a nitrogen component contained in ammonia as an ammonia gas decomposition product by decomposing an ammonia component in an ammonia-containing gas by nitrifying bacteria, the nitrogen recovery device including:
  (A) a microorganism decomposition tank equipped with a nitrifying bacterium carrier supporting nitrifying bacteria, the microorganism decomposition tank decomposing the ammonia gas under an oxygen-containing atmosphere,
  (B) an ammonia-containing gas supply unit to supply the ammonia-containing gas to the microorganism decomposition tank,
  (C) a water supply unit to supply water to the microorganism decomposition tank,
  (D) a water discharge line to draw off water including the ammonia gas decomposition product generated in the microorganism decomposition tank from the microorganism decomposition tank,
  (E) a storage tank to temporarily stores the water including the ammonia gas decomposition product discharged from the water discharge line,
  (F) a retreating line to connect the storage tank and the microorganism decomposition tank to carry the water including the ammonia gas decomposition product from the storage tank to the microorganism decomposition tank,
  (G) a circulation unit to circulate the water including the ammonia gas decomposition product through the microorganism decomposition tank, the water discharge line, the storage tank, and the retreating line, and
  (H) a recovery unit to collect all or a portion of the water including the ammonia gas decomposition product (circulating water) with a predetermined concentration of nitrate ion from the storage tank.

In one embodiment of the nitrogen recovery device in the present invention, the nitrifying bacterium carrier is an inorganic porous body and/or an inorganic fibrous body, e.g., glass foam. However, even if the carrier is made of organic matter, a porous body and a fibrous body from organic matter such as plastic, rubber or resin which does not generate an odor by decay can be used.

In one embodiment of the nitrogen recovery device in the present invention, the microorganism decomposition tank is of a vertically oriented countercurrent contact type to supply an ammonia-containing gas from a lower part side and to supply water from an upper part side.

In one embodiment of the nitrogen recovery device in the present invention, the nitrifying bacteria include ammonia-oxidizing bacteria (AOB) and nitrite-oxidizing bacteria (NOB).

The present invention to solve the problem is also achieved by a product, such as a liquid fertilizer and a solid fertilizer produced by extracting the nitrogen component therefrom, obtained by using water including an ammonia gas decomposition product recovered in the foregoing nitrogen recovery method (for example, by recovering nitric acid in circulating water by crystallization).

Effects of the Invention

According to the present invention, a nitrogen component can be recovered with high efficiency from ammonia gas generated in e.g., livestock production facilities, compost depot, and sewage treatment plants, and recovered nitrogen is retained as nitrate ion in water at a high concentration and thus can be effectively utilized as a fertilizer as it is.

BRIEF DESCRIPTION OF DRAWINGS

FIG. 1 is a diagram which schematically illustrates a structure in one embodiment of the nitrogen recovery device of the present invention.

PREFERRED MODE FOR CARRYING OUT THE INVENTION

The present invention will now be described in detail by way of embodiments thereof.
<Nitrogen Recovery Device>
FIG. 1 is a diagram which schematically shows a structure in one embodiment of the nitrogen recovery device in the present invention.

The nitrogen recovery device according to one embodiment in the present invention shown in FIG. 1 includes an ammonia gas source tank 10, and a microorganism decomposition tank 20, which is a reaction field to decompose an ammonia-containing gas generated in the ammonia gas source tank 10. The nitrogen recovery device also has a water supply line 30, which supplies water from the upper part side of the microorganism decomposition tank 20; a water discharge line 40, which draws out water having passed through the inside of the microorganism decomposition tank 20 from the bottom side of the microorganism decomposition tank 20; a storage tank 50, which temporarily stores water discharged from the water discharge line 40; and a retreating line 70, which connects this storage tank 50 and the upper part side of the microorganism decomposition tank 20, and carries water stored in the storage tank 50 to the microorganism decomposition tank again. A circulation pump (e.g., lifting pump) 60 is arranged in the storage tank 50 as a circulation unit, which circulates the water through the microorganism decomposition tank 20, the water discharge line 40, the storage tank 50 and the retreating line 70. In addition, the storage tank 50 is provided with a nitric acid aqueous solution recovery line 80 having a switching valve as a recovery unit, which, when water in the storage tank 50 has a predetermined concentration of nitrate ion, recovers the water from the storage tank 50. A pH sensor 91, which measures the pH of water in the storage tank, is further arranged in the storage tank 50, and is electrically connected to a pH controller 90 outside the tank. The pH controller 90 has a structure in which the actuation of a release pump (not shown) in either of an alkaline liquid tank 101 and an acid liquid tank 102 can be controlled by a selector switch (not shown), and when a pH value measured in the pH sensor 91 is not a predetermined pH value, an alkaline liquid or an acid liquid is carried from the alkaline liquid tank 101 or the acid liquid tank 102 to the storage tank 50 through a pH adjuster supply line 100 to automatically adjust the pH of water to the predetermined pH value. Each component will now be described in more detail.

(Ammonia-Containing Gas Supply Unit)

The ammonia gas source tank 10 is not an essential structure in the nitrogen recovery device according to the present invention, and is not particularly limited as long as it generates an ammonia-containing gas as a part of an ammonia-containing gas supply unit, which supplies the ammonia-containing gas to the microorganism decomposition tank 20.

For example, the ammonia gas source tank 10 can have a structure in which in the process of livestock excreta treatment such as the process of composting treatment of livestock manure, an ammonia-containing gas is generated by ammonia stripping from sewage obtained by solid-liquid separation, and wastewater with a high concentration of ammoniacal nitrogen as obtained by organic decomposition of sewage. In addition, it is not required to limit the type of waste fluid to livestock waste liquid, and, for example, the ammonia gas source tank can have a structure in which ammonium ion included in waste fluid discharged from food plants or generated during treating processes is generated by ammonia stripping.

It should be noted that in the nitrogen recovery device according to the present invention, the ammonia-containing gas supply unit is not limited only to the embodiment having the ammonia gas source tank 10 described above in any way. For example, the ammonia-containing gas has generally an odor, and examples thereof can include odor gas in a variety of facilities, e.g., livestock manure composting treatment as described above, odor gas in livestock industry, odor gas in composting and wastewater treatment, odor gas during the process of industrial waste treatment and the like, or exhaust gas in a variety of manufacturing processes. The ammonia-containing gas supply unit may supply these ammonia-containing gases directly from the sources thereof or indirectly from parts in which the gases are temporarily captured and recovered.

In addition to ammonia, these ammonia-containing gases may include hydrogen sulfide, mercaptans, amines, aldehydes, fatty acids, aromatic compounds, and the like. The upper limit of the total amount of ammonia in the ammonia-containing gas supplied by the ammonia-containing gas supply unit in the present invention is not particularly limited, but is for example, 2000 mg or less, 1800 mg or less, 1600 mg or less, 1400 mg or less, 1200 mg or less, 1000 mg or less, 800 mg or less, 700 mg or less, 600 mg or less, and about 500 mg or less per day with respect to 1 L of packed volume of the nitrifying bacterium carrier. In addition, the lower limit thereof is not particularly limited, but is preferably 10 mg or more, more preferably 50 mg or more, and further preferably 100 mg or more because there is a risk that the activity of nitrifying bacteria will be reduced when ammonia gas supply is completely stopped for a long period of time. However, even when the ammonia gas supply is temporarily stopped over a period of some days to about two weeks, if the supply is resumed, that is not a big problem. In addition, a stop of ammonia gas supply is not a big problem also when ammonium ion remains in circulating water.

In the nitrogen recovery device according to one embodiment in the present invention shown in FIG. 1, the ammonia-containing gas generated from the ammonia gas source tank 10 is carried to the microorganism decomposition tank 20 through an ammonia-containing gas supply line 11, which is from the ammonia gas source tank 10 to the vicinity of the lower end of the microorganism decomposition tank 20, by the air suction pump 12.

(Microorganism Decomposition Tank)

The microorganism decomposition tank 20, which is a reaction field to decompose the ammonia-containing gas, can retain sufficient amounts of water and nitrifying bacteria, and is also packed with a nitrifying bacterium carrier 21 to obtain sufficient gas contact efficiency. Nitrifying bacteria are supported to this nitrifying bacterium carrier 21.

It should be noted that the nitrogen recovery device according to one embodiment in the present invention shown in FIG. 1 has a structure in which a carrier holding plate (not shown) with air permeability (and liquid permeability) is arranged in the vicinity of the bottom of this microorganism decomposition tank 20 so that the section surface of the bottom opening of the microorganism decomposition tank 20 will be blocked, and the nitrifying bacterium carrier 21 can be packed in the microorganism decomposition tank 20 by accumulating the nitrifying bacterium carrier 21 on the carrier holding plate.

In addition, in the nitrogen recovery device according to one embodiment in the present invention shown in FIG. 1, at least a part of the upper part of the microorganism decomposition tank 20 is opened. Water (circulating water) is supplied into the microorganism decomposition tank 20 from the water spray unit 31 in the atmosphere, which is under an oxygen-containing atmosphere, in the upper part of the microorganism decomposition tank 20 as described below. It should be noted that in the nitrogen recovery method and device in the present invention, microorganism decomposition is commonly carried out under an oxygen-containing atmosphere such as in the atmosphere. Therefore, it is not required that e.g., an oxygen supply step and an oxygen share device be separately located; however, such step and device can be included as required.

Therefore, as described above, the ammonia-containing gas supplied from the ammonia-containing gas supply line 11 flows into the inside of the microorganism decomposition tank 20 from the bottom opening side of the microorganism decomposition tank 20, and comes in touch with the nitrifying bacterium carrier 21 in a state retaining supplied water while the ammonia-containing gas passes upward through the microorganism decomposition tank 20. The ammonia component in the ammonia-containing gas is dissolved in water retained by the nitrifying bacterium carrier 21, and then gas after deammoniation is discharged from the upper opening of the microorganism decomposition tank 20 to the outside of the system.

Meanwhile, as described in detail below, ammonia dissolved in water retained by the nitrifying bacterium carrier 21 is decomposed by two types or more of nitrifying bacteria on the nitrifying bacterium carrier 21, and an ammonia gas decomposition product generated by the decomposition is then washed out with water (circulating water) supplied into the microorganism decomposition tank 20. Water (circulating water) containing the ammonia gas decomposition product is drawn off from the bottom opening of the microorganism decomposition tank 20, and carried to the circulating water storage tank 50 through the water discharge line 40.

It is desired that the microorganism decomposition tank 20 have a vertically oriented shape, more specifically a shape having a larger size in the vertical direction than in the horizontal direction, for uniform and efficient contact between the ammonia-containing gas and the nitrifying bacterium carrier 21 arranged in the inside thereof, and be of the countercurrent contact type, in which the ammonia-containing gas is supplied from the lower part side and water is supplied from the upper part side, but the microorganism decomposition tank 20 is not particularly limited thereto.

(Nitrifying Bacterium Carrier)

As the amount of water which can be retained by the nitrifying bacterium carrier 21 packed in the microorganism decomposition tank 20 (the amount of water absorption) increases, the amount of ammonia gas which can be absorbed increases. However, when the amount of water is too large, oxygen supply required for the nitrification reaction becomes insufficient, which causes a reduction in the rate of the nitrification reaction. In addition, the denitrification reaction occurs to change nitric acid into nitrogen gas under anaerobic conditions, in which oxygen supply is insufficient. As a result, the recovery rate of nitric acid is reduced, and thus the nitrifying bacterium carrier preferably include a material which can retain a proper water balance. In addition, for example, organic materials such as chaff and wood chips are not desired at least to obtain stable characteristics for a long period of time because an organic component generated by decay thereof promotes denitrification. Therefore, inorganic materials which can maintain a moderate water retention ability and air permeability are preferred, and specific examples thereof include inorganic porous bodies and/or inorganic fibrous bodies, e.g., glass foam, rock wool, glass wool, pearlite, pumice, Oya stone, and the like. However, even if the material is organic matter, a porous body and a fibrous body from organic matter such as plastic, rubber or resin which does not generate an odor by decay can be used. Among these, glass foam is particularly preferred.

The "glass foam" in the present description indicates porous bulk glass which contains a foam material in glass and has been foamed by heating. The material of glass foam is not particularly limited, and examples thereof can include soda-lime glass, borate glass, phosphate glass, and the like, or mixed glass of these glasses, having e.g., waste glass as a raw material, and the like. Among these, glass foam including soda-lime glass is preferred.

The pore volume of glass foam is preferably 0.6 cm$^3$/g or more, more preferably 0.8 cm$^3$/g or more, further preferably 1.0 cm$^3$/g or more, particularly preferably 1.2 cm$^3$/g or more, especially preferably 1.4 cm$^3$/g or more, and most preferably 1.6 cm$^3$/g or more to maintain a moderate water retention ability and air permeability. On the other hand, when the pore volume is too large, the proportion of voids in glass foam increases, and there is a risk that durability will be reduced, and thus the upper limit thereof may be, for example, 4.0 cm$^3$/g or less (3.5 cm$^3$/g or less, 3.0 cm$^3$/g or less, 2.5 cm$^3$/g or less). The pore volume is measured by a mercury intrusion method.

As the specific surface area of glass foam increases, the glass foam can support more nitrifying bacteria, and thus the specific surface area is desirably 3.0 m$^2$/g or more, more preferably 4.0 m$^2$/g or more, further desirably 5.0 m$^2$/g or more, particularly preferably 10 m$^2$/g or more, especially preferably 20 m$^2$/g or more, and most preferably 40 m$^2$/g or more. On the other hand, the upper limit thereof is not particularly restricted, and may be 150 m$^2$/g or less (100 m$^2$/g or less, 80 m$^2$/g or less, 60 m$^2$/g or less). The specific surface area is measured by a mercury intrusion method.

In order to maintain the amount of water, which can absorb the ammonia component, in the microorganism decomposition tank, the percentage of water content of glass foam is preferably 5% or more, desirably 7% or more, particularly 10% or more, more preferably 20% or more, further preferably 25% or more, and particularly preferably 30% or more as the water content per 1 L of packed volume. It may be 40% or more, for example 50% or more, or 60% or more as required. On the other hand, in order to sufficiently supply oxygen required for nitrification, the upper limit thereof can be 90% or less, more preferably 80% or less, and further preferably 70% or less. The percentage of water content u (%) of the nitrifying bacterium carrier is measured by the following method.

First, a nitrifying bacterium carrier (e.g., glass foam) is taken in a 100 mL container to a level container, and the taken nitrifying bacterium carrier is immersed in water in an amount which can completely immerse the carrier (e.g., 1 L) overnight or longer to allow the nitrifying bacterium carrier to sufficiently absorb water. When the dry weight (g) of the nitrifying bacterium carrier before absorbing water is W1, and the weight (g) of the nitrifying bacterium carrier after absorbing water is W2, (W2−W1) is the weight (g) of water absorbed by the nitrifying bacterium carrier, and when 1 g of water is converted into 1 mL, the percentage of water content u (vol %) is calculated by the following formula:

$$u(\%) = \{\text{volume (mL) of water absorbed by nitrifying bacterium carrier/volume } (mL) \text{ of container in which nitrifying bacterium carrier is taken}\} \times 100 = \{(W2-W1)/100\} \times 100.$$

For example, when the dry weight of the nitrifying bacterium carrier before absorbing water W1 is 10 g, and the weight of the nitrifying bacterium carrier after absorbing water W2 is 25 g, the weight of water absorbed by the nitrifying bacterium carrier is (25−10=) 15 g. When it is converted into a volume, the value is 15 mL, and thus the percentage of water content u (%) is (15/100)×100, which is 15%.

As described above, the nitrifying bacterium carrier is preferably a porous body such as glass foam and a fibrous body such as rock wool, and the shape and size thereof are not particularly restricted. For example, a porous body in almost spherical, almost spindle, or almost cube shape, or a porous body in a random shape, i.e. an uneven and unstable porous body may be used, and a fibrous body with a fiber diameter of 0.1 μm to 10 μm, and particularly 3 μm to 8 μm can be also used. In order to uniformly pack the carrier in the microorganism decomposition tank 20, the shape of the porous body is preferably almost spherical and almost spindle shapes, and the like, or shapes close thereto, and the particle diameter (short diameter) is preferably above 1 mm and 50 mm or less, more preferably above 3 mm and 20 mm or less, and particularly preferably above 3 mm and 10 mm or less. When the particle diameter of the nitrifying bacterium carrier (e.g., glass foam) is more than 50 mm, there is a risk that it will be difficult to uniformly pack the carrier in the microorganism decomposition tank 20. In addition, because gaps between particles increase, circulating water supplied from the upper part easily pass between particles of the nitrifying bacterium carrier, and the contact rate (or contact time) with nitrifying bacteria supported to the nitrifying bacterium carrier tends to be reduced. Meanwhile, when the particle diameter of the nitrifying bacterium carrier is smaller than 1 mm, gaps between the particles of the nitrifying bacterium carrier packed in the microorganism decomposition tank 20 become insufficient when the carrier is packed in the microorganism decomposition tank 20, and there is a risk that it will be difficult to secure sufficient air permeability and liquid permeability, and there is also a risk that it will be difficult to uniformly cause the decomposition reaction of ammonia gas on the whole packed layer of the nitrifying bacterium carrier. Additionally, the nitrifying bacterium carrier with a particle diameter of smaller than 1 mm flows outside the microorganism decomposition tank 20 simultaneously with applying the liquid, and there is also a risk that the device will be broken down.

The particle diameter of a porous body can be measured, for example, by known methods such as laser diffraction and phase Doppler methods. From practical viewpoints, however, a porous body is preferably used after being classified by screening defined in e.g., JIS Z 8815-1994 [Test sieving—General requirements] and used. For example, particles classified by the above JIS method into above 1 mm and 1.4 mm or less, above 1.4 mm and 2 mm or less, above 2 mm and 2.8 mm or less, above 2.8 mm and 4 mm or less, above 4 mm and 5.6 mm or less, above 5.6 mm and 8 mm or less, above 8 mm and 11.2 mm or less, above 11.2 mm and 16 mm or less, or above 16 mm and 22.4 mm or less, and the like, or those classified into a desired range such as above 1 mm and 2 mm or less, or above 3 mm and 20 mm or less can be used. It should be noted that the "particle diameter with above X mm and Y mm or less" in the present invention specifically means the range of particle diameter in which a particle nitrifying bacterium carrier (particles) can pass through a sieve with a sieve opening of Y mm and cannot pass through a sieve with an opening of X mm.

The "rock wool" in the present description indicates artificial mineral fibers produced by melting e.g., natural rocks such as basalt or blast furnace slag at high temperature and making fibers.

In the nitrifying bacterium carrier 21, the packed height when the packed volume of the nitrifying bacterium carrier 21 is 1 L is preferably 10 cm or more, more preferably 20 cm or more, further preferably 30 cm or more, particularly preferably 40 cm or more, and especially preferably 50 cm or more so that the ammonia-containing gas will uniformly spread across the carrier packed layer. As the packed height increases, it is required to carry the ammonia-containing gas at a higher pressure to allow the gas to pass through the microorganism decomposition tank 20 packed with the nitrifying bacterium carrier 21, and thus in order to obtain good reaction efficiency, it is desired to pack the carrier in the microorganism decomposition tank 20 so that the upper limit thereof will be 200 cm or less, preferably 150 cm or less, and more preferably 100 cm or less. The "packed volume of the nitrifying bacterium carrier is 1 L" indicates as a volume the amount of the nitrifying bacterium carrier when the nitrifying bacterium carrier is packed in a 1 L container to a level container.

(Nitrifying Bacteria)

Nitrifying bacteria are supported to the nitrifying bacterium carrier 21. The nitrifying bacteria include at least ammonia-oxidizing bacteria (AOB) and nitrite-oxidizing bacteria (NOB) in decomposition treatment of the ammonia-containing gas.

When the nitrifying bacteria are supported to the nitrifying bacterium carrier 21, for example, activated sludge, e.g., activated sludge derived from piggery wastewater treated by an activated sludge method in piggery wastewater treatment facilities, and the like can be used as seed bacteria. The activated sludge is not particularly limited as long as it include AOB and NOB as described above, but, for example, when the abundance of AOB to all microorganisms in the seed bacteria (hereinafter, may be simply referred to as AOB abundance) is 0.5% or more, preferably 1.0% or more, more preferably 2.0% or more, further preferably 4.0% or more, or particularly preferably 8.0% or more by the metagenome analysis of the seed bacteria, the nitrifying bacterial flora can be relatively quickly established. In addition, when the abundance of NOB (hereinafter, may be simply referred to as "NOB abundance") is preferably 0.1% or more, more preferably 0.2% or more, further preferably 0.4% or more, or particularly preferably 1.0% or more, the nitrification rate can be further increased. The upper limit of the abundance of AOB and NOB is not particularly restricted, both may exist at 50% each or at about 30% each. As the ratio of both, AOB is preferably higher, the ratio of AOB:NOB is more preferably 2:1 to 30:1, particularly about 3:1 to 20:1, which is advantageous to promote nitrification. It should be noted that "%" to show the abundance of AOB and NOB is the "relative percentage to the number of all microorganisms existing in the carrier". The prior culture of activated sludge may be carried out before supporting nitrifying bacteria. In particular, for example, when sludge after being collected is stored under refrigeration, the state of bacteria can be restored by prior culture.

Activated sludge in piggery wastewater treatment facilities, for example, is aerobically cultured in a nitrifying bacterium medium (e.g., Juhler S., Revsbech N. P., Schramm A., Herrmann M., Ottosen L. D. M. and Nielsen L. P. (2009): Distribution and rate of microbial processes in ammonia-loaded air filter biofilm. Appl. Environ. Microbiol. 75:3705-3713. or Kruemmeland Heinz (1982): Effect of organic matter on growth and cell yield of ammonia-oxidizing bacteria. Arch. Microbiol. 133:50-54) at 15 to 40° C., particularly 20 to 35° C. for one day to several weeks, and the obtained culture can be used as activated sludge.

The amount of activated sludge added varies depending on the AOB abundance, but activated sludge is added, for example, at a proportion of 5 to 500 vol % with respect to the packed volume of the nitrifying bacterium carrier 21, such as 5 vol %, 10 vol %, 20 vol %, 30 vol %, 50 vol %, 70 vol %, 100 vol %, 150 vol %, 200 vol %, 300 vol %, 400 vol %, and 500 vol %. It should be noted that nitrifying bacteria supported to the nitrifying bacterium carrier 21 pass through the ammonia-containing gas to cause the decomposition reaction of ammonia, and thus the bacteria increase and decrease. Therefore, the initial amount of seed bacteria added is not a very important parameter.

The ammonia-oxidizing bacteria (AOB) are not particularly limited, and examples thereof include bacteria belonging to Nitrosomonadaceae or *Nitrosomonas, Nitrosococcus, Nitrosospira, Nitrosolobus, Brevibacillus*, and *Xanthomonas*.

More specific and non-limiting examples thereof can include *Nitrosomonas europaea, Nitrosomonas marina,*

*Nitrosomonas oligotropha, Nitrosomonas communis*, and the like as *Nitrosomonas; Nitrosococcus mobilis*, and the like as *Nitrosococcus; Nitrosospira multiformis, Nitrosospira tenuis*, and the like as *Nitrosospira; Nitrosolobus multiformis*, and the like as *Nitrosolobus*.

The nitrite-oxidizing bacteria (NOB) are not particularly limited, and examples thereof include bacteria belonging to Nitrococaceae or *Nitrococcus, Nitrobacter*, and *Nitrospira*.

More specific and non-limiting examples thereof can include *Nitrococcus mobilis*, and the like as *Nitrococcus; Nitrobacter winogradskyi, Nitrobacter alkalicus, Nitrobacter vulgaris, Nitrobacter hamburgensis*, and the like as *Nitrobacter; Nitrospira marina, Nitrospira moscoviensis*, and the like as *Nitrospira*.

When the ammonia-containing gas generated in the ammonia gas source tank 10 flows into the microorganism decomposition tank 20 and comes into contact with the nitrifying bacterium carrier 21 in the state retaining water under an oxygen-containing atmosphere, ammonia-oxidizing bacteria (AOB) grow in the nitrifying bacterium carrier 21. Ammonium ion ($NH_4^+$) dissolved in water is oxidized to nitrite ion ($NO_2^-$) by the ammonia-oxidizing bacteria (AOB) under aerobic conditions as shown in the chemical equation (1) below:

$$NH_4^+ + 1.5O_2 \rightarrow NO_2^- + 2H^+ + H_2O \quad (1).$$

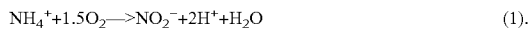

As nitrite ion ($NO_2^-$) in water increases, nitrite-oxidizing bacteria (NOB) grow, and nitrite ion ($NO_2^-$) is oxidized to nitrate ion ($NO_3^-$) by the nitrite-oxidizing bacteria (NOB) under an oxygen-containing atmosphere as shown in the chemical equation (2) below:

$$NO_2^- + 0.5O_2 \rightarrow NO_3^- \quad (2).$$

When the above chemical equations (1) and (2) are combined, the reaction is:

$$NH_4^+ + 2O_2 \rightarrow NO_3^- + 2H^+ + H_2O.$$

It is generally said that in the nitrification reaction by the ammonia-oxidizing bacteria (AOB) and nitrite-oxidizing bacteria (NOB) as described above, the generation of nitrite ion by oxidation of ammonia is a rate-determining step, which determines the reaction rate, and the reaction from nitrite ion to nitrate ion rapidly proceeds. In the nitrogen recovery device and nitrogen recovery method according to the present invention, however, unlike the above the generation reaction of nitrite ion by oxidation of ammonia is not particularly rate determining. When both of the ammonia-oxidizing bacteria (AOB) and nitrite-oxidizing bacteria (NOB) exist at certain proportions on the nitrifying bacterium carrier, ammonia is quickly decomposed into nitrite ion, and nitrous acid into nitrate ion, and the proportions of ammonia and nitrite ion remaining in water are reduced, and the proportion of nitrate ion can be increased.

In the nitrogen recovery device according to the present invention, nitrate ion, which is an ammonia gas decomposition product produced by nitrifying bacteria supported to the nitrifying bacterium carrier 21 as described above, is dissolved together with unreacted ammonium ion and nitrite ion in water in the microorganism decomposition tank 20, then washed out with water supplied to the microorganism decomposition tank 20, drawn off from the bottom opening of the microorganism decomposition tank 20, and carried to the circulating water storage tank 50 through the water discharge line 40. Water including the ammonia gas decomposition product temporarily stored in the circulating water storage tank 50 is supplied again as circulating water into the microorganism decomposition tank 20 through the retreating line 70 by the circulation pump 60 as described above. Therefore, when the nitrogen recovery device according to the present invention is put in action, and the ammonia-containing gas is continuously sent from the ammonia gas source tank 10 to continue the reaction, the concentration of nitrate ion (and nitrite ion) in the circulating water naturally increases over time.

It has been known that such increases in nitrate ion and nitrite ion generally cause a reduction in the activity of nitrifying bacteria, particularly ammonia-oxidizing bacteria (AOB), and cause a decrease in ammonia-oxidizing bacteria, and finally the decomposition reaction of ammonia is reduced.

A specific action mechanism thereof has not been sufficiently clarified yet; however, it was revealed that in the structure of the nitrogen recovery device according to the present invention, surprisingly, even when the device was put in action for a long time, and the concentration of nitrate ion in circulating water was relatively high, the oxidation reaction of fresh ammonium ion sufficiently proceeded in the microorganism decomposition tank 20. It was also found that even when the concentration of nitrate ion in water reached, for example, 5000 mg/L or more, suitably 5000 mg/L to 200000 mg/L, certain proportions of AOB and NOB existed, and the decomposition of the ammonia component proceeded. In this respect, it was considered that as the reaction proceeded, nitric acid resistant AOB and NOB grew, and the decomposition of ammonium ion into nitric acid was maintained.

It should be noted that such feature was similarly observed even when nitrifying bacteria initially added as seed bacteria to the nitrifying bacterium carrier 21 or activated sludge was changed, and thus it is considered that the feature is peculiar to the structure of the nitrogen recovery device according to the present invention, or the steps of the nitrogen recovery method according to the present invention.

In the present invention, the distribution state of ammonia-oxidizing bacteria (AOB) and nitrite-oxidizing bacteria (NOB) in the nitrifying bacterium carrier 21 is not particularly limited, and AOB and NOB may exist almost equally in the whole nitrifying bacterium carrier 21, or AOB and NOB may exist separately in each of specific sites of the nitrifying bacterium carrier 21. It should be noted that as one preferred distribution state in the nitrifying bacterium carrier 21, AOB is unevenly distributed in a place on the lower part side of the microorganism decomposition tank 20, i.e. the side on which the ammonia-containing gas flows into the microorganism decomposition tank 20, and NOB is unevenly distributed on the side higher than the above. In this distribution state, each reaction of the ammonia-oxidizing bacteria (AOB) and nitrite-oxidizing bacteria (NOB) in the microorganism decomposition tank 20 can be more efficiently carried out. Such distribution state of the ammonia-oxidizing bacteria (AOB) and nitrite-oxidizing bacteria (NOB) can be relatively commonly formed when the nitrogen recovery device of the present invention is put in action, and AOB and NOB grow in the nitrifying bacterium carrier 21 as time passes to an extent.

(Water Discharge Line, Circulating Water Storage Tank)

The structure of the water discharge line 40 is not particularly limited, and e.g., any shape and any line length may be used as long as water including an ammonia decomposition product flowing out from the bottom of the microorganism decomposition tank 20 (circulating water) can be certainly led to the circulating water storage tank 50. As the structure of the circulating water storage tank 50, as long as a predetermined amount of circulating water can be stored with respect to the volume of the microorganism decomposition tank 20 (nitrifying bacterium carrier 21), respects other than e.g., the shape and site arranged are not particularly limited. It should be noted that the nitrification reaction by the ammonia-oxidizing bacteria (AOB) and nitrite-oxidizing bacteria (NOB) as described above proceeds under aerobic conditions, and, when denitrifying bacteria exist, a nitrogen component captured in water by the denitrification reaction can be emitted in the atmosphere under anaerobic conditions, and thus it is desired to have a structure in which the flow channel of circulating water, such as the water discharge line 40 and circulating water storage tank 50, can be also aerated if possible.

It is desired that the circulating water storage tank 50 include water temperature adjustment systems such as a cooler and a heater, but the tank is not limited thereto, and the temperature of circulating water is preferably adjusted to a temperature range suitable for the activity of nitrifying bacteria, specifically for example a range of 10 to 60° C., and moreover more suitably 15 to 50° C., particularly 20 to 40° C. In the ammonia-oxidizing bacteria (AOB) and nitrite-oxidizing bacteria (NOB), furthermore, temperature ranges optimum for the activity thereof are different to some extent depending on bacterial species thereof, and thus the degree of reaction progresses between the oxidation reaction of ammonium ion by the ammonia-oxidizing bacteria (AOB) and the oxidation reaction of nitrite ion by the nitrite-oxidizing bacteria (NOB) can be also adjusted by more precisely adjusting the temperature.

(Water Supply Unit)

The nitrogen recovery device according to one embodiment in the present invention shown in FIG. 1 has a water supply line 30, which has a switching valve and is connected to the course of the retreating line 70, to initially supply fresh water to the nitrogen recovery device. However, the water supply unit which supplies water to the microorganism decomposition tank 20 in the nitrogen recovery device of the present invention is not limited to the structure of the water supply line as shown in FIG. 1 in any way as long as it can initially supply fresh water to the nitrogen recovery device, and then can switch to circulating water. In addition to this, any structure can be formed, such as a structure in which fresh water can be simply supplied to the circulating water storage tank 50, or a structure in which water can be supplied from the upper part side of the microorganism decomposition tank 20, separately from the retreating line 70. In addition, the nitrogen recovery device according to one embodiment in the present invention is provided with the water spray unit 31, which is connected to the water supply line 30 and retreating line 70 as described above, and sprays water (circulating water) to the decomposition tank 20 from the upper part side of the microorganism decomposition tank 20; however, the structure thereof is not particularly limited as long as water (circulating water) can be almost evenly sprayed to the whole nitrifying bacterium carrier 21 in the microorganism decomposition tank 20. In addition, it is not particularly required to arrange this water spray unit 31 itself.

(Retreating Line, Circulation Unit)

In the nitrogen recovery device of the present invention, the structures of a retreating line 70, which circulates and supplies circulating water from the circulating water storage tank 50 to the microorganism decomposition tank 20, and a circulation pump 60 as a circulation unit are not particularly limited to the structures shown in the embodiment in FIG. 1, and an optional structure can be used as long as water can be circulated.

It should be noted that circulating water may be continuously supplied to the nitrifying bacterium carrier 21 packed in the microorganism decomposition tank 20; however, it is more preferred that the water be intermittingly supplied. That is, when water is continuously supplied, the surface of the nitrifying bacterium carrier 21, a reaction field, is always covered with water depending on the amount supplied, and therefore there is a risk that the rate of the nitrification reaction will be reduced by insufficient oxygen supply, and there is also a risk that anaerobic conditions will be caused to develop the denitrification reaction.

(Nitric Acid Aqueous Solution Recovery Line)

The nitrogen recovery device according to one embodiment in the present invention shown in FIG. 1 is provided with a nitric acid aqueous solution recovery line 80 having a switching valve as a recovery unit, which recovers water from the storage tank 50 when water in the storage tank 50 has a predetermined concentration of nitrate ion. However, the structure of this recovery unit is not particularly limited as long as, when the reaction in the nitrogen recovery device proceeds, it is closed to maintain water circulation, and, when water has a predetermined concentration of nitrate ion, it can recover all or a portion of circulating water from a water circulation line. It may be located on any site or have any mechanism. When it is detected that water reaches a predetermined concentration of nitrate ion, water may be recovered by automatic or manual actuation.

(pH Adjustment Mechanism)

The nitrogen recovery device according to one embodiment in the present invention shown in FIG. 1 is provided with a pH adjustment mechanism for adjusting the pH of circulating water, which includes a pH sensor 91, a pH controller 90, an alkaline liquid tank 101, an acid liquid tank 102, and a pH adjuster supply line 100 as described above. In the nitrogen recovery device according to the present invention, such pH adjustment mechanism is preferably arranged; however, it is not an essential component, and the structure of the pH adjustment mechanism is also not limited to the embodiment shown in FIG. 1 in any way, and a variety of known aspects can be used. In the pH adjustment mechanism shown in FIG. 1, for example, either of alkali and acid can be added, and even when pH moves to acidity or even when pH moves to alkalinity, the pH can be adjusted; however, a structure in which only alkali can be added can be also used. That is, generally, when water including ammonium ion dissolved therein is oxidized by the ammonia-oxidizing bacteria (AOB), overall, there is a high tendency to reduce the pH of water, and the oxidation of ammonia is inhibited by a reduction of pH. Therefore, even a form in which only alkali can be added, can practically adjust the pH of water. It should be noted that alkali and acid used are not particularly limited, and, for example, alkali metal hydroxides such as sodium hydroxide and potassium hydroxide, alkali earth metal hydroxides such as calcium hydroxide and magnesium hydroxide, lime hydrate and ultra-alkaline water including any of the above, and the like as alkali, and hydrochloric acid, sulfuric acid, nitric acid, phosphoric acid, and the like as acid can be used.

<Nitrogen Recovery Method>

The nitrogen recovery method according to the present invention is a nitrogen recovery method for recovering a nitrogen component contained in ammonia as an ammonia gas decomposition product by decomposing an ammonia component in an ammonia-containing gas by nitrifying bacteria using a nitrogen recovery device having the structure as described above, the method being characterized by supplying circulating water to a microorganism decomposition tank 20 equipped with the nitrifying bacterium carrier 21 supporting nitrifying bacteria to maintain the nitrifying bacterium carrier 21 in a wet state; allowing the ammonia-containing gas to pass through the nitrifying bacterium carrier 21 in the wet state under an oxygen-containing atmosphere; dissolving an ammonia component in the ammonia-containing gas in the circulating water, together with an ammonia gas decomposition product produced by the nitrifying bacteria, and continuing to decompose the ammonia-containing gas while accumulating the ammonia gas decomposition product in the circulating water; and collecting all or a portion of the circulating water to recover the ammonia gas decomposition product, when the concentration of nitrate ion as an ammonia decomposition product in the circulating water is increased to 5000 mg/L or more and reaches a predetermined concentration.

Using a nitrogen recovery device having the structure as described above, even when the concentration of nitrate ion in circulating water becomes higher, that is, the concentration of nitrate ion is 5000 mg/L or more, more preferably 30000 mg/L or more, and further preferably 60000 mg/L or more, the decomposition reaction of an ammonia-containing gas by nitrifying bacteria can be maintained with high efficiency under conditions that at least ammonia-oxidizing bacteria (AOB) and nitrite-oxidizing bacteria (NOB) exist, and when the concentration of nitrate ion is increased to 5000 mg/L or more and reaches a predetermined concentration such as 10000 mg/L or more, 15000 mg/L or more, 20000 mg/L or more, or 25000 mg/L or more, circulating water can be recovered. In particular, by recovering circulating water when the concentration of nitrate ion is 5000 mg/L to 200000 mg/L, more preferably 30000 mg/L to 150000 mg/L, and further preferably 60000 mg/L to 100000 mg/L, a nitric acid aqueous solution with a high concentration, which can be effectively utilized, for example, as a liquid fertilizer, is obtained. Of nitrogen contained in the injected ammonia-containing gas, 30% or more, preferably 40% or more, more preferably 50% or more, further preferably 60% or more, particularly preferably 70% or more, and especially preferably 80% or more based on the mass of nitrogen atom can be recovered as nitrogen included in nitrate ion.

It should be noted that in the nitrogen recovery method according to the present invention, even after recovering circulating water including nitrate ion at a high concentration as described above, nitrifying bacteria supported to the nitrifying bacterium carrier 21 can effectively act. Therefore, when fresh circulating water is supplied into the system, and the ammonia-containing gas is allowed to pass through to resume the decomposition treatment, the decomposition reaction of the ammonia-containing gas efficiently proceeds as is the case of the prior treatment. Accordingly, nitrogen can be repeatedly recovered from the ammonia-containing gas without exchanging the nitrifying bacterium carrier 21, or the nitrifying bacteria supported thereto. The fresh circulating water may be water, or activated sludge containing nitrifying bacteria, or the like. Because the activity of nitrifying bacteria can be reduced by dramatically changing environmental conditions including circulating water, the proportion of circulating water, which is recovered and exchanged at once, is preferably less than 100% of the total amount of circulating water, more preferably 90% or less, further preferably 80% or less, particularly preferably 70% or less, and most preferably 60% or less, while it is desired that the proportion be at least 20% or more of the total amount of circulating water, more preferably 30% or more, further preferably 40% or more, and most preferably 50% or more for effective recovery and exchange. However, circulating water, which is recovered and exchanged at once, may be 100% of the total amount of circulating water.

According to the present invention, even when the concentration of nitrate ion is 5000 mg/L or more, and moreover 60000 mg/L or more, the decomposition reaction of an ammonia-containing gas by nitrifying bacteria can be maintained with high efficiency as described above. Therefore, even if only a portion of circulating water is recovered and exchanged, and an ammonia-containing gas is injected under conditions that the concentration of nitrate ion in exchanged circulating water is for example 3000 mg/L or more, and moreover 10000 mg/L or more, the ammonia-containing gas is efficiently decomposed, and the concentration of nitrate ion in circulating water can be significantly higher than the concentration at the start point of injecting the ammonia-containing gas. In the above nitrogen recovery method, the present invention also includes a nitrogen recovery method in which, when the concentration of nitrate ion in circulating water is increased by 5000 mg/L or more from the concentration immediately after the start of operation, which starts injecting the ammonia-containing gas, and reaches a predetermined high concentration, all or a portion of the circulating water is recovered as an ammonia gas decomposition product.

In the nitrogen recovery method of the present invention, in order that the decomposition reaction of the ammonia-containing gas by nitrifying bacteria will be allowed to stably proceed even when the concentration of nitrate ion accumulated in circulating water is higher as described above, it is desired that conditions as described below be each within the ranges defined, but this is not particularly limited.

That is, the material of the nitrifying bacterium carrier 21 is preferably an inorganic material which can maintain a moderate water retention ability and air permeability as described above, particularly desirably glass foam.

In addition, the temperature of the nitrifying bacterium carrier 21 is preferably 10° C. or higher, more preferably 15° C. or higher, further preferably 20° C. or higher, and particularly preferably 25° C. or higher to maintain the activity of microorganisms. The temperature may be 30° C. or higher, further 35° C. or higher, and particularly 37° C. or higher as required. On the other hand, an excessive increase causes a reduction in the activity of microorganisms, also promotes the vaporization of ammonia gas, and can be a cause to reduce a nitrogen recovery rate. Therefore, in order that the active reaction by nitrifying bacteria will proceed, and a high nitrogen recovery rate will be achieved, the upper limit thereof is 60° C. or lower, more preferably 55° C. or lower, further preferably 50° C. or lower, particularly preferably 45° C. or lower, especially preferably 40° C. or lower. It should be noted that the method for adjusting the temperature of the nitrifying bacterium carrier 21 is not particularly limited, and a method in which the temperature is directly adjusted using an electric heater, a method in which circulating water with a temperature adjusted by e.g., a method described below is supplied to the nitrifying bacterium carrier 21, and a method in which cooling water is separately supplied can be used. As is the case of the above, the temperature of circulating water is preferably 10° C. or higher, more preferably 15° C. or higher, and further preferably 20° C. or higher. On the other hand, the upper limit thereof be 60° C. or lower, more preferably 55° C. or lower, further preferably 50° C. or lower, particularly preferably 45° C. or lower, and especially desirably 40° C. or lower. The temperature of circulating water is 10 to 60° C., more preferably 15 to 50° C., further 20 to 40° C., and particularly 25 to 35° C., which are effective to activate nitrifying bacteria. It should be noted that the method for adjusting the temperature of circulating water is not particularly limited, and a method in which an electric immersion heater is put in circulating water can be used.

The packed height of the nitrifying bacterium carrier 21 when the packed volume of the nitrifying bacterium carrier 21 is 1 L is preferably 10 cm or more, more preferably 20 cm or more, further preferably 30 cm or more, particularly preferably 40 cm or more, and especially preferably 50 cm as described above. On the other hand, the nitrifying bacterium carrier 21 is desirably packed in the microorganism decomposition tank 20 so that the upper limit thereof will be 200 cm or less, more preferably 150 cm or less, and further preferably 100 cm or less.

Furthermore, the percentage of water content of the nitrifying bacterium carrier 21 in the microorganism decomposition tank 20 is preferably 5% or more per L of packed volume of the nitrifying bacterium carrier 21, desirably 7% or more, particularly desirably 10% or more, more preferably 20% or more, further preferably 25% or more, and particularly preferably 30% or more as described above. It may be 40% or more, for example 50% or more, or 60% or more as required. When the percentage of water content is for example 10% or more, particularly 20% or more, the ability of capturing ammonia gas can be also increased, and the deodorization rate can be also increased particularly when it is about 30% or more. In order that aerobic conditions will be maintained to promote the nitrification reaction, it is desired that the upper limit thereof be 90% or less, more preferably 80% or less, and further preferably 70% or less.

In order to maintain the activity of nitrifying bacteria including ammonia-oxidizing bacteria (AOB) and nitrite-oxidizing bacteria (NOB) well, the lower limit of pH of circulating water adjusted is preferably pH 5.0 or more, more preferably 5.5 or more, further preferably 6.0 or more, particularly preferably 6.2 or more, especially preferably 6.5 or more, and most preferably 6.8 or more. When the pH of circulating water is about 5.5 or more, and particularly about 6.5 or more, there is also an advantage that remaining ammonia is significantly suppressed. On the other hand, the upper limit thereof is preferably 9.0 or less, more preferably 8.8 or less, further preferably 8.6 or less, particularly preferably 8.4 or less, especially preferably 8.2 or less, and most preferably 8.0 or less. When pH is above 9.0, there is a risk that the nitrification activity will be reduced, and there is also a risk that ammonia will be easily volatilized to leak the ammonia gas outside the device. The pH of circulating water means the permanent pH of circulating water, and it is not problematic that pH is locally and temporarily outside the above range until an alkali or an acid added to adjust pH becomes uniform in circulating water. When an ultrahigh concentration of ammonia gas flows in a mass for a short period of time, pH can be above 9; however, a temporary pH increase does not develop a problem.

In order that the nitrifying bacterium carrier 21 will be in a fully wet state, and ammonium ion from the ammonia-containing gas passing through, and nitrite ion and nitrate ion generated from the nitrification reaction will be stably retained and accumulated in circulating water, it is desired that the amount of circulating water be preferably 0.01 times or more higher than the packed volume of the nitrifying bacterium carrier 21 in the nitrogen recovery device, more preferably 0.05 times or more, further 0.5 times or more, and particularly 0.5 to 10 times.

For the purpose of obtaining the nitrifying bacterium carrier in a moderately wet state, retaining the activity of nitrifying bacteria, also supplying water to dissolve the ammonia component, and further washing out an ammonia decomposition product, the circulation amount of circulating water per hour is preferably 50 mL/h or more per 1 L of packed volume of the nitrifying bacterium carrier 21, more preferably 100 mL/h or more, further preferably 200 mL/h or more, particularly preferably 400 mL/h or more, especially preferably 1000 mL/h or more, and most desirably 5000 mL/h or more. On the other hand, in order to retain moderate oxygen supply, the upper limit thereof is preferably 50000 mL/h or less and more preferably 30000 mL/h or less.

Furthermore, in order that the reaction will proceed under aerobic conditions, and in order to supply oxygen consumed in the oxidization reaction by the ammonia-oxidizing bacteria (AOB) and nitrite-oxidizing bacteria (NOB), and also prevent a reduction in a nitrogen recovery rate by denitrification when circulating water becomes an anaerobic state, the aeration amount in circulating water is preferably 0.5 L/min or more with respect to 1 L of circulating water, more preferably 1 L/min or more, further preferably 1.5 L/min or more, particularly preferably 2.0 L/min or more, especially preferably 3.0 L/min or more, and most preferably 4.0 L/min or more. On the other hand, because there is a risk that excessive aeration will promote the vaporization of ammonia, the upper limit thereof is preferably 10 L/min or less with respect to 1 L of circulating water, more preferably 8.0 L/min or less, and further preferably 6.0 L/min or less. It should be noted that circulating water can be aerated, for example, by an aeration pump; however, aeration is not necessarily required, for example, when an ammonia-containing gas supplied by an ammonia-containing gas supply unit includes a sufficient amount of oxygen (air).

EXAMPLES

The present invention will now be described in more detail by way of examples thereof.

Example 1

An ammonia-containing gas was decomposed using a nitrogen recovery device having the structure as shown in FIG. 1.

Glass foam (Bub Glass G0004 manufactured by Murakami Corporation), 350 g (corresponding to 1 L of packed volume), was used as a nitrifying bacterium carrier, and 3 L (corresponding to 300 vol % of packed volume of glass foam) of activated sludge (containing AOB and NOB) obtained from an activate sludge tank in a pig farm in Saitama Prefecture was added thereto as seed bacteria.

An ammonia-containing gas was allowed to pass through the nitrogen recovery device on the conditions that the temperature of the nitrifying bacterium carrier 21 was 28 to 33° C. (measured by inserting a thermometer from the upper part of the microorganism decomposition tank), the temperature of circulating water was 28 to 33° C., the packed height was 20 cm when the packed volume of the nitrifying bacterium carrier 21 was 1 L, the percentage of water content of the nitrifying bacterium carrier 21 was 30% in the microorganism decomposition tank 20, the pH of the circulating water was 7.0 to 9.0 (when pH was not within the range, pH was automatically adjusted by adding a 0.5 N aqueous solution of sodium hydroxide in the pH controller), the amount of the circulating water was three times the volume of the nitrifying bacterium carrier 21, the circulation amount of the circulating water per hour was 200 mL/h per 1 L of packed volume of the nitrifying bacterium carrier 21, and the aeration amount in the circulating water was 4 L/min with respect to 3 L of the circulating water. The ammonia-containing gas was allowed to pass through by introducing gas in a tank with a high concentration of ammonia water into the device by a suction pump. The injected amount of ammonia was about 350 mg/day in terms of the mass of nitrogen atom.

The circulating water was collected in an amount of 10 mL on each predetermined day, and the concentration of each ion in the circulating water, ammonium ion, nitrite ion, and nitrate ion, was measured by a colorimetric analysis method. These measurement values were converted into the concentration of nitrogen atom to calculate the concentration of nitrogen in each ion, and based on the calculation results, the ratio of nitrogen forms of nitrogen atom in the circulating water was found. These results are shown in Table 1.

reaction is not easy to proceed; however, in the present example, such tendency was not observed. It is suggested from the results until the 28th day, the oxidation of ammonia by AOB initially proceeds, and the oxidation of nitrous acid by NOB then proceeds.

It should be noted that a rate of recovering nitrogen in the injected ammonia-containing gas as nitrogen in circulating water (nitrogen recovery rate) largely varied depending on measurement days because ions in circulating water could be intermittently captured by the nitrifying bacterium carrier; however, when an increment in the weight of nitrogen atom in 3 L of circulating water was calculated based on the concentration of nitrogen ion on the first day and the 84th day, the value was 19545 mg (=(13/18+15/46+29886/62-319/18)×14×3), and it was verified that about 66% of nitrogen in the injected ammonia (total amount=350 mg/day×84 days=29400 mg) could be recovered. Additionally, almost 100% of the recovered nitrogen was nitrate nitrogen ($N(NO_3^-)$). When 50% of the total amount of circulating water (1.5 L in 3 L) was exchanged for water after the 84th day, and the operation was continued again, it was also verified by the test continued thereafter that nitrate

TABLE 1

Test results in Example 1 (Carrier: Bub Glass G0004, water content percentage 30%)

|  |  | Elapsed days (day) | | | | | | | | | |
|---|---|---|---|---|---|---|---|---|---|---|---|
|  |  | 0 | 7 | 13 | 21 | 28 | 32 | 42 | 53 | 70 | 84 |
| Ion concentration * | $NH_4^+$ | 319 | 286 | 1 | 1 | 6 | 5 | 6 | 7 | 4 | 13 |
|  | $NO_2^-$ | 0 | 483 | 2999 | 3787 | 0 | 7 | 3 | 16 | 4 | 15 |
|  | $NO_3^-$ | 0 | 58 | 286 | 1328 | 6640 | 6972 | 9823 | 25844 | 28208 | 29886 |
| Nitrogen form ratio # | $N(NH_4^+)$ | 100 | 58 | 0 | 0 | 0 | 0 | 0 | 0 | 0 | 0 |
|  | $N(NO_2^-)$ | 0 | 39 | 93 | 79 | 0 | 0 | 0 | 0 | 0 | 0 |
|  | $N(NO_3^-)$ | 0 | 3 | 7 | 21 | 100 | 100 | 100 | 100 | 100 | 100 |

* unit: mg/L
unit: %

From the test results shown in Table 1, the concentration of nitrate ion ($NO_3^-$) in the circulating water was 6640 mg/L on the 28th day after the start of the test, which was significantly above 5000 mg/L, and increased to 29886 mg/L on the 84th day. It was indicated that ammonia was decomposed for deodorization, and the obtained nitrate nitrogen ($N(NO_3^-)$) could be recovered at a high concentration in accordance with the present invention. As described above, it has been generally known that the activity of nitrifying bacteria, particularly AOB, is reduced due to increases in the concentration of nitrate ion ($NO_3^-$) and nitrite ion ($NO_2^-$), and the ammonia decomposition ion with an increased concentration equal to that before exchange was accumulated in circulating water.

Examples 2 to 3

The same operation as in Example 1 was carried out except that rock wool (the percentage of water content 86%: Example 2) or pearlite (the percentage of water content 44%: Example 3) was used in place of glass foam as the nitrifying bacterium carrier. The test results are shown in Table 2.

TABLE 2

|  |  | Elapsed days (day) | | | | | | | | | |
|---|---|---|---|---|---|---|---|---|---|---|---|
|  |  | 0 | 7 | 13 | 21 | 28 | 32 | 42 | 53 | 70 | 84 |
| Test results in Example 2 (Carrier: rock wool, water content percentage 86%) | | | | | | | | | | | |
| Ion concentration * | $NH_4^+$ | 319 | 30 | 9 | 208 | 235 | 54 | 6 | 18 | 5 | 13 |
|  | $NO_2^-$ | 0 | 144 | 667 | 3415 | 4432 | 4221 | 1 | 15 | 5 | 6 |
|  | $NO_3^-$ | 0 | 0 | 0 | 407 | 1680 | 2373 | 8587 | 17292 | 21659 | 30265 |
| Nitrogen form ratio # | $N(NH_4^+)$ | 100 | 34 | 3 | 13 | 10 | 2 | 0 | 0 | 0 | 0 |
|  | $N(NO_2^-)$ | 0 | 66 | 97 | 80 | 70 | 69 | 0 | 0 | 0 | 0 |
|  | $N(NO_3^-)$ | 0 | 0 | 0 | 7 | 20 | 29 | 100 | 100 | 100 | 100 |
| Test results in Example 3 (Carrier: pearlite, water content percentage 44%) | | | | | | | | | | | |
| Ion concentration * | $NH_4^+$ | 319 | 342 | 7 | 20 | 115 | 123 | 13 | 17 | 3 | 3 |
|  | $NO_2^-$ | 0 | 416 | 2426 | 4628 | 6826 | 6404 | 2306 | 12 | 4 | 5 |
|  | $NO_3^-$ | 0 | 0 | 0 | 949 | 526 | 1952 | 4496 | 17657 | 18748 | 24381 |

TABLE 2-continued

|  |  | Elapsed days (day) | | | | | | | | |
|---|---|---|---|---|---|---|---|---|---|---|
|  |  | 0 | 7 | 13 | 21 | 28 | 32 | 42 | 53 | 70 | 84 |
| Nitrogen form ratio # | N(NH$_4^+$) | 100 | 68 | 1 | 1 | 4 | 4 | 1 | 0 | 0 | 0 |
|  | N(NO$_2^-$) | 0 | 32 | 99 | 86 | 91 | 78 | 40 | 0 | 0 | 0 |
|  | N(NO$_3^-$) | 0 | 0 | 0 | 13 | 5 | 18 | 59 | 100 | 100 | 100 |

\* unit: mg/L
unit: %

It is found from the test results shown in Table 2 that in Example 2 using rock wool as the nitrifying bacterium carrier, the concentration of nitrate ion in circulating water is 8587 mg/L on the 42nd day, which is significantly above 5000 mg/L, and 30265 mg/L on the 84th day, which is above 30000 mg/L. When the nitrogen recovery rate was calculated from the concentrations of ion on the first day and the 84th day in the same manner as in Example 1, it was also verified that it is above 66%. It is also found that in Example 3 using pearlite as the nitrifying bacterium carrier, the concentration of nitrate ion in circulating water is 17657 mg/L on the 53rd day, which is significantly above 5000 mg/L, and 24381 mg/L on the 84th day, which is above 20000 mg/L. It was further verified that the nitrogen recovery rate was also above 50%.

Examples 4 to 5

In Example 4, the same operation as in Example 1 was carried out except that activated sludge was retained at 32° C. for two days to culture seed bacteria, and the injected amount of ammonia was changed to about 380 mg/day in terms of the mass of nitrogen atom. In Example 5, the same operation as in Example 4 was carried out except that activated sludge obtained from an activate sludge tank in a pig farm in Shizuoka Prefecture was used as seed bacteria, and cultured at 32° C. for 8 days, the injected amount of ammonia was changed to about 425 mg/L in terms of the mass of nitrogen atom, and the temperature of the nitrifying bacterium carrier and the temperature of circulating water were adjusted to 35° C. and 32° C., respectively. It should be noted that in Example 5, the abundance of AOB and NOB to all microorganisms was analyzed by 16S rRNA metagenome analysis. The test results in Examples 4 and 5 are shown in Table 3.

TABLE 3

Test results in Example 4

|  |  | Elapsed days (day) | | | | | | | | |
|---|---|---|---|---|---|---|---|---|---|---|
|  |  | 0 | 3 | 7 | 15 | 18 | 24 | 39 | 49 | 56 | 60 |
| Ion concentration *1 | NH$_4^+$ | 118 | 229 | 112 | 13 | 15 | 499 | 312 | 181 | 200 | 5 |
|  | NO$_2^-$ | 1550 | 2095 | 2585 | 4023 | 3421 | 200 | 49 | 16 | 33 | 6 |
|  | NO$_3^-$ | 158 | 210 | 158 | 594 | 2811 | 6005 | 19999 | 26203 | 28771 | 24531 |
| Nitrogen form ratio *2 | N(NH$_4^+$) | 15 | 21 | 10 | 1 | 1 | 22 | 5 | 2 | 2 | 0 |
|  | N(NO$_2^-$) | 79 | 74 | 86 | 89 | 62 | 3 | 0 | 0 | 0 | 0 |
|  | N(NO$_3^-$) | 6 | 5 | 4 | 10 | 37 | 75 | 95 | 98 | 98 | 100 |

Test results in Example 5

|  |  | Elapsed days (day) | | | | | | | | |
|---|---|---|---|---|---|---|---|---|---|---|
|  |  | 0 | 7 | 10 | 18 | 25 | 31 | 38 | 47 | 74 | 95 |
| Ion concentration *1 | NH$_4^+$ | 385 | 131 | 58 | 34 | 228 | 138 | 123 | 700 | 778 | 1373 |
|  | NO$_2^-$ | 96 | 2596 | 2995 | 3177 | 8 | 0 | 200 | 42 | 104 | 40 |
|  | NO$_3^-$ | 0 | 0 | 61 | 681 | 2018 | 14802 | 26503 | 40450 | 56211 | 62458 |
| Nitrogen form ratio *2 | N(NH$_4^+$) | 91 | 11 | 5 | 2 | 28 | 3 | 2 | 6 | 5 | 7 |
|  | N(NO$_2^-$) | 9 | 89 | 94 | 84 | 0 | 0 | 1 | 0 | 0 | 0 |
|  | N(NO$_3^-$) | 0 | 0 | 1 | 14 | 72 | 97 | 97 | 94 | 95 | 93 |
| Abundance *3 | AOB | 1.3 | 7.4 | — | 27.5 | 26.2 | 23.4 | — | — | — | — |
|  | NOB | 0 | 0.04 | — | 0.4 | 1.3 | 2.1 | — | — | — | — |

*1 unit: mg/L
*2 unit: %
*3 Abundance in all microorganisms (%)

From the test results shown in Table 3, the concentration of nitrate ion was 6005 mg/L on the 24th day, which increased by 5000 mg/L or more from the value on the first day of the test (158 mg/L), and 28771 mg/L on the 56th day, which increased close to 30000 mg/L, in Example 4. It was also verified that when the nitrogen recovery rate on the 60th day was calculated in the same manner as in Example 1, it was about 65%. In Example 5, the concentration of nitrate ion was 14802 mg/L on the 31st day, which was significantly above 5000 mg/L, 40450 mg/L on the 47th day, which was significantly above 30000 mg/L, and 62458 mg/L on the 95th day, which was more than 60000 mg/L. In both Examples 4 and 5, activated sludge cultures are used as nitrifying bacteria, and thus e.g., nitrite ion is detected from the start of the test.

It can be seen from the changes in the abundance of AOB and NOB measured in Example 5, and the concentration of each ion that from the 0th day to the 7th day the proportion of AOB was a little more than 7% and simultaneously the concentration of nitrite ion increased, while the concentration of nitrate ion began to increase from the 18th day on which the proportion of NOB was 0.4%, and significantly increased after the 25th day on which the proportion of NOB exceeded 1%.

Example 6

The same operation as in Example 4 was carried out except that the number of days for culture of activated sludge was 22 days, 3 L of circulating water, obtained by mixing 1.2 L of water recovered after the same device as in Example 1 had been operated for 150 days or more on the same conditions as in Example 1, was used, and the temperature and pH of the circulating water were not adjusted (the temperature was an environmental temperature), aeration was not carried out, and the injected amount of ammonia was changed to about 280 mg/day in terms of the mass of nitrogen atom. The test results are shown in Table 4.

obviously higher than in Examples 4 and 5. In addition, nitrate nitrogen ($N(NO_3^-)$) was 56 to 80% of the recovered nitrogen after the 32nd day, and ammonia nitrogen ($N(NH_4^+)$) was 20 to 39%. It is suggested that e.g., temperature and pH are preferably adjusted to recover a high concentration of nitrate ion and suppress the amount of ammonia.

Example 7

The same operation as in Example 4 was carried out except that glass foam (Bub Glass G0001 manufactured by Murakami Corporation) with a water content percentage of 9% was used as the nitrifying bacterium carrier, microorganisms used in other Examples were used as seed bacteria, and the injected amount of ammonia was changed to about 340 mg/day in terms of the mass of nitrogen atom. The

TABLE 4

| | | Examples | | | | | | | |
|---|---|---|---|---|---|---|---|---|---|
| | | Test results in Example 6 (without condition adjustment) | | | | | | | Example 4 |
| | | Elapsed days (day) | | | | | | | |
| | | 0 | 9 | 15 | 22 | 32 | 39 | 47 | 57 | 39@ |
| Ion concentration * | $NH_4^+$ | 122 | 507 | 846 | 1004 | 2964 | 1837 | 1787 | 4990 | 312 (194) |
| | $NO_2^-$ | 778 | 1043 | 697 | 2749 | 878 | 878 | 1 | 0 | 49 (−1501) |
| | $NO_3^-$ | 11248 | 10089 | 9323 | 11476 | 14699 | 18476 | 25393 | 30253 | 19999 (19841) |
| Nitrogen form ratio # | $N(NH_4^+)$ | 3 | 13 | 22 | 19 | 39 | 24 | 20 | 36 | 5 |
| | $N(NO_2^-)$ | 8 | 11 | 7 | 20 | 5 | 5 | 0 | 0 | 0 |
| | $N(NO_3^-)$ | 89 | 76 | 71 | 61 | 56 | 71 | 80 | 64 | 95 |

* unit: mg/L
unit: %
@ the values in brackets: increments from 0th day

In Example 6, pH was not adjusted, and therefore the pH of circulating water after 22 days was reduced to around 6.0, and reduced to around 5.5 after 47 days. Despite an initial nitrate ion concentration of 10000 mg/L or more even in Example 6 in which e.g., temperature conditions were not adjusted, the accumulation of nitrate ion was continued, and an increment in the concentration of nitrate ion from the first day was 7228 mg/L (=18476−11248 mg/L) on the 39th day, which was above 5000 mg/L. Compared to the 49th day in Example 4 and the 47th day in Example 5, the concentration of nitrate ion on the 47th day in Example 6 was equal thereto, while the concentration of ammonium ion was microorganisms were recovered from the surface of glass foam by suspending the glass foam used in a nitrogen recovery device, which had been operated on the same conditions as in Example 1 for 100 days or more, in circulating water. After recovery 3 L of liquid was put in the nitrogen recovery device provided with 0.9 L of the above glass foam, and circulated for 12 days to spread the microorganisms to the glass foam, and the circulating water was then 10-fold diluted. After that, the same operation as in Example 4 was carried out to measure the concentration of each ion. The results are shown in Table 5.

TABLE 5

| | | Example 7 (water content percentage 9%) | | | | | | |
|---|---|---|---|---|---|---|---|---|
| | | Elapsed days (day) | | | | | | |
| | | 0 | 6 | 13 | 20 | 27 | 34 | 41 |
| Ion concentration * | $NH_4^+$ | 50 | 228 | 67 | 18 | 0 | 0 | 1 |
| | $NO_2^-$ | 0 | 336 | 64 | 5 | 6 | 2 | 0 |
| | $NO_3^-$ | 2155 | 5542 | 7123 | 9546 | 9662 | 15482 | 16652 |
| Nitrogen form ratio # | $N(NH_4^+)$ | 7 | 12 | 3 | 1 | 0 | 0 | 0 |
| | $N(NO_2^-)$ | 0 | 7 | 1 | 0 | 0 | 0 | 0 |
| | $N(NO_3^-)$ | 93 | 82 | 96 | 99 | 100 | 100 | 100 |

* unit: mg/L
unit: %

In Example 7, an increment in the concentration of nitrate ion from the first day was 7391 (=9546-2155) mg/L on the 20th day, which was above 5000 mg/L, and 7507 (=9662-2155) mg/L on the 27th day, and moreover 14497 (=16652-2155) mg/L on the 41st day. The reason why the concentration of nitric acid was high on the first day is because circulating water from another device was used as culture fluid. In the present Example, even after the concentration of nitric acid was above 5000 mg/L, much of injected ammonia was oxidized to nitric acid, and ammonia nitrogen was little left in circulating water, and thus it can be said that the activity of nitrification is sufficiently displayed. It was indicated that even when the percentage of water content of the carrier is 9%, nitrate ion can be recovered at a high concentration. However, because the amount of water in a carrier has an effect on the ability of capturing ammonia gas which passes through the device, when the injected amount of ammonia gas is increased, a carrier with a low percentage of water content cannot sufficiently capture ammonia gas, and there is a risk that the nitrogen recovery rate will be reduced.

Examples 8 to 11

The same operation as in Example 1 was carried out except that three nitrogen recovery devices, which had been operated on the same conditions as in Example 1 for 200 days or more, were used, the total amount of fresh circulating water was made to 2.8 L by adding ion exchange water to 10% of circulating water remaining in the devices, and while adjusting the lower limit of pH thereof to 6.5, the injected amount of ammonia was changed to about 200 to 300 mg/day (in terms of the mass of nitrogen atom). That is, using glass foam (Bub Glass G0004 described above, the percentage of water content 30%) which had already supported activated sludge (nitrifying bacteria), the test, in which the lower limit of pH of circulating water was 6.5, was carried out in n=3, (Example 8). The three nitrogen recovery devices after completion of the test in Example 8 were used, fresh circulating water was made to 2.8 L by adding ion exchange water to 10% of circulating water remaining in the devices, and while adjusting the lower limit of pH thereof to 6.0, the same test as in Example 8 was carried out (Example 9). The same test as in Example 9 was carried out except that the three nitrogen recovery devices after completion of the test in Example 9 were used, and the lower limit of pH of circulating water was adjusted to 5.5 (Example 10). The same test as in Examples 9 and 10 was carried out except that the three nitrogen recovery devices after completion of the test in Example 10 were used, and the lower limit of pH of circulating water was adjusted to 5.0 (Example 11). The test results in each Example are shown in Table 6. It should be noted that the values in Table 6 are mean values of n=3.

TABLE 6

| | | Examples | | | | | | | |
|---|---|---|---|---|---|---|---|---|---|
| | | Example 8 (pH = 6.5) Injected amount of ammonia: about 210*[3] | | | | Example 9 (pH = 6.0) (Injected amount of ammonia: about 210*[3]) | | | |
| | | Elapsed days (day) | | | | | | | |
| | | 0 | 7 | 14 | 20 | 0 | 8 | 15 | 22 |
| Ion concentration *[1] | $NH_4^+$ | 11 | 90 | 28 | 74 | 3 | 50 | 255 | 314 |
| | $NO_2^-$ | 3 | 4 | 0 | 8 | 0 | 0 | 2 | 3 |
| | $NO_3^-$ | 3406 | 6359 | 9816 | 11790 | 2906 | 4956 | 7375 | 8424 |
| Nitrogen form ratio *[2] | $N(NH_4^+)$ | 1 | 4 | 1 | 2 | 0 | 3 | 10 | 10 |
| | $N(NO_2^-)$ | 0 | 0 | 0 | 0 | 0 | 0 | 0 | 0 |
| | $N(NO_3^-)$ | 99 | 96 | 99 | 98 | 100 | 97 | 90 | 90 |
| | | Examples | | | | | | | |
| | | Example1 10 (pH = 5.5) Injected amount of ammonia: about 280*[3] | | | | Example 11 (pH = 5.0) Injected amount of ammonia: about 240*[3] | | | |
| | | Elapsed days (day) | | | | | | | |
| | | 0 | 7 | 14 | 20 | 0 | 7 | 14 | 21 |
| Ion concentration *[1] | $NH_4^+$ | 4 | 79 | 191 | 139 | 18 | 258 | 486 | 697 |
| | $NO_2^-$ | 0 | 0 | 142 | 4 | 0 | 25 | 1 | 33 |
| | $NO_3^-$ | 3907 | 6212 | 8284 | 9587 | 3144 | 3909 | 6033 | 6305 |
| Nitrogen form ratio *[2] | $N(NH_4^+)$ | 0 | 3 | 6 | 4 | 2 | 17 | 20 | 23 |
| | $N(NO_2^-)$ | 0 | 0 | 2 | 0 | 0 | 1 | 0 | 0 |
| | $N(NO_3^-)$ | 100 | 97 | 92 | 96 | 98 | 82 | 80 | 77 |

*[1] unit: mg/L
*[2] unit: %
*[3] Mass of nitrogen in injected ammonia gas, unit: mg/day From the test results shown in Table 6, in Example 11 in which the lower limit of pH of circulating water was adjusted to 5.0, the concentration of nitrate ion was 6033 mg/L on the 14th day, which was above 5000 mg/L, and it was verified that the nitrification reaction proceeded. However, in view of the concentration of nitrate ion at the start of the experiment, an increment in the concentration in Example 11 was low, 3161 (=6305-3144) mg/L, even on the 21st day, which was less than 5000 mg/L, and compared to Examples 8 to 10, in which the lower limit of pH was adjusted to 5.5 or more, particularly Example 8, in which the lower limit of pH was adjusted to 6.5, the extent of nitrification was obviously low. In Examples 8 to 10, 90% or more of the recovered nitrogen was nitrate nitrogen. Contrarily, it was verified that in Example 11, nitrate nitrogen of the recovered nitrogen was around 80%, and ammonia nitrogen was 17 to 23%. It was indicated that the pH of circulating water was preferably adjusted to 5.5 or more, particularly 6.5 or more.

Examples 12 to 13

The same test as in Example 8 was carried out except that the three nitrogen recovery devices after completion of the test in Example 11 were used, 2.8 L of fresh circulating water was used, the temperature of the circulating water was adjusted to 20° C., the lower limit of pH was adjusted to 7.0, the temperature of glass foam was not adjusted, and the injected amount of ammonia was changed to about 300 mg/day in terms of the mass of nitrogen atom (Example 12). The same test as in Example 12 was carried out except that one of the nitrogen recovery devices after completion of the test in Example 12 was used, and the temperature of circulating water was adjusted to 15° C. (Example 13). The test results in each Example were shown in Table 7.

the order of operation at 15° C. (Example 13)<operation at 20° C. (Example 12)<operation at 30° C. (Example 8). It was verified that after 21 days, around 99% of nitrogen recovered from injected ammonia was nitrate nitrogen in both Examples 12 and 13.

It was indicated that according to the present invention, even when the temperature of circulating water was reduced to 20° C. or around 15° C., nitrate ion could be recovered from ammonia at a high concentration, and could be effectively utilized as nitrate nitrogen unlike conventional techniques in which it is discharged as nitrogen gas.

EXPLANATION OF REFERENCE NUMERALS

10: Ammonia gas source tank
11: Ammonia-containing gas supply line
12: Air suction pump
20: Microorganism decomposition tank
21: Nitrifying bacterium carrier
30: Water supply line
31: Water spray unit
40: Water discharge line
50: Circulating water storage tank
60: Circulation pump
70: Retreating line
80: Nitric acid aqueous solution recovery line
90: pH controller
91: pH sensor

TABLE 7

| | | Examples | | | | | | | |
|---|---|---|---|---|---|---|---|---|---|
| | | 12 (Circulating water 20° C.) | | | | | 13 (Circulating water 20° C.) | | |
| | | Elapsed days (day) | | | | | | | |
| | | 0 | 7 | 14 | 21 | 28 | 0 | 7 | 21 |
| Ion concentration *1 | $NH_4^+$ | 7 | 23 | 46 | 10 | 48 | 0 | 0 | 1 |
| | $NO_2^-$ | 0 | 87 | 207 | 56 | 16 | 0 | 0 | 0 |
| | $NO_3^-$ | 3619 | 4823 | 5968 | 9122 | 11965 | 3833 | 5490 | 8861 |
| Nitrogen form ratio *2 | $N(NH_4^+)$ | 1 | 2 | 2 | 0 | 2 | 0 | 0 | 0 |
| | $N(NO_2^-)$ | 0 | 3 | 3 | 1 | 0 | 0 | 0 | 0 |
| | $N(NO_3^-)$ | 99 | 95 | 95 | 99 | 98 | 100 | 100 | 100 |

\* unit: mg/L
\# unit: %

As shown in Table 7, in Examples 12 and 13, increments in the concentration of nitrate ion from the first day to the 21st day were 5503 (=9122-3619) mg/L, and 5028 (=8861-3833) mg/L, respectively, and both were above 5000 mg/L. It was found that these values were far from the value on the 20th day in Example 8, in which the temperature of circulating water was adjusted to 30° C. (concentration 11790 mg/L, an increment from the first day 8384 mg/L; although the following cannot be stated positively because not only the temperatures but also pH of circulating water were different, considering that the pH of circulating water is most preferably 6.8 or more, it is presumed that a higher concentration of nitrate ion than in Example 8 is obtained when the lower limit of pH of circulating water is 7.0 and the temperature is adjusted to 30° C.); however, nitrification proceeded even after the concentration of nitrate ion was above 5000 mg/L. In particular, in Example 12 in which the temperature of circulating water was 20° C., the concentration of nitrate ion was 11965 after 28 days, which was above 10000 mg/L. The extent of progress of nitrification was in 100: pH adjuster supply line
101: Alkaline liquid tank
102: Acid liquid tank

The invention claimed is:

1. A nitrogen recovery method for recovering a nitrogen component contained in ammonia as an ammonia gas decomposition product by decomposing an ammonia component in an ammonia-containing gas using nitrifying bacteria, the method comprising:
supplying circulating water to a microorganism decomposition tank equipped with a nitrifying bacterium carrier supporting nitrifying bacteria to maintain the nitrifying bacterium carrier in a wet state;
allowing the ammonia-containing gas to pass through the nitrifying bacterium carrier in the wet state under an oxygen-containing atmosphere dissolving an ammonia component in the ammonia-containing gas in the circulating water, together with an ammonia gas decomposition product produced by the nitrifying bacteria, and continuing to decompose the ammonia-containing gas while accumulating the ammonia gas decomposition product in the circulating water; and collecting all or a portion of the circulating water to recover the ammonia gas decomposition product, when a concentration of nitrate ion as an ammonia decomposition product in the circulating water is increased to 5000 mg/L or more and reaches a predetermined concentration, wherein the nitrifying bacteria supported to be the nitrifying bacterium carrier comprise ammonia-oxidizing bacteria and nitrite-oxidizing bacteria.

2. The nitrogen recovery method according to claim 1, wherein the nitrifying bacterium carrier is an inorganic porous body and/or an inorganic fibrous body.

3. The nitrogen recovery method according to claim 1, wherein the nitrifying bacterium carrier is glass foam.

4. The nitrogen recovery method according to claim 1, wherein a percentage of water content of the nitrifying bacterium carrier in the microorganism decomposition tank is 5% to 90%.

5. The nitrogen recovery method according to claim 1, wherein an amount of the circulating water supplied to the microorganism decomposition tank per 1 L of packed volume of the nitrifying bacterium carrier is 50 to 50000 mL/h.

6. The nitrogen recovery method according to claim 1, wherein the circulating water is aerated, and the amount of aeration per 1 L of the circulating water is 0.5 to 10 L/min.

7. The nitrogen recovery method according to claim 1, wherein the circulating water is maintained at a pH of 5.0 to 9.0 and at a temperature of 10° C. to 60° C.

8. The nitrogen recovery method according to claim 1, further comprising supplying fresh circulating water to a system to resume decomposing the ammonia-containing gas after collecting all or a portion of the circulating water to recover the ammonia gas decomposition product when the concentration of nitrate ion as the ammonia decomposition product in the circulating water is increased to 5000 mg/L or more and reaches a predetermined concentration.

9. The nitrogen recovery method according to claim 1, wherein all or a portion of the circulating water is collected to recover the ammonia gas decomposition product, when the concentration of nitrate ion in the circulating water is increased by 5000 mg/L or more from a concentration at a start point of allowing the ammonia-containing gas to pass through.

10. A nitrogen recovery method for recovering a nitrogen component contained in ammonia as an ammonia gas decomposition product by decomposing an ammonia component in an ammonia-containing gas using nitrifying bacteria, the method comprising:

supplying circulating water to a microorganism decomposition tank equipped with a nitrifying bacterium carrier supporting nitrifying bacteria to maintain the nitrifying bacterium carrier in a wet state at a percentage of water content of the nitrifying bacterium carrier in the microorganism decomposition tank being 5% to 90%;

allowing the ammonia-containing gas to pass through the nitrifying bacterium carrier in the wet state under an oxygen-containing atmosphere;

dissolving an ammonia component in the ammonia-containing gas in the circulating water, together with an ammonia gas decomposition product produced by the nitrifying bacteria, and continuing to decompose the ammonia-containing gas while accumulating the ammonia gas decomposition product in the circulating water; and collecting all or a portion of the circulating water to recover the ammonia gas decomposition product, when a concentration of nitrate ion as an ammonia decomposition product in the circulating water is increased to 5000 mg/L or more and reaches a predetermined concentration.

11. A nitrogen recovery method for recovering a nitrogen component contained in ammonia as an ammonia gas decomposition product by decomposing an ammonia component in an ammonia-containing gas using nitrifying bacteria, the method comprising:

supplying circulating water to a microorganism decomposition tank equipped with a nitrifying bacterium carrier supporting nitrifying bacteria to maintain the nitrifying bacterium carrier in a wet state, wherein the nitrifying bacterium carrier is glass foam;

allowing the ammonia-containing gas to pass through the nitrifying bacterium carrier in the wet state under an oxygen-containing atmosphere;

dissolving an ammonia component in the ammonia-containing gas in the circulating water, together with an ammonia gas decomposition product produced by the nitrifying bacteria, and continuing to decompose the ammonia-containing gas while accumulating the ammonia gas decomposition product in the circulating water; and collecting all or a portion of the circulating water to recover the ammonia gas decomposition product, when a concentration of nitrate ion as an ammonia decomposition product in the circulating water is increased to 5000 mg/L or more and reaches a predetermined concentration.

* * * * *

UNITED STATES PATENT AND TRADEMARK OFFICE
CERTIFICATE OF CORRECTION

PATENT NO. : 12,343,678 B2
APPLICATION NO. : 17/642368
DATED : July 1, 2025
INVENTOR(S) : Akira Fujino et al.

It is certified that error appears in the above-identified patent and that said Letters Patent is hereby corrected as shown below:

In the Claims

Column 30, Claim 1, Line 63, please insert a --;-- so the line reads as "oxygen-containing atmosphere;
dissolving an ammonia component in the ammonia-containing gas in the circulating water,".

Signed and Sealed this
Twenty-sixth Day of August, 2025

Coke Morgan Stewart
*Acting Director of the United States Patent and Trademark Office*